United States Patent [19]

Main et al.

[11] Patent Number: 4,932,975
[45] Date of Patent: Jun. 12, 1990

[54] VERTEBRAL PROSTHESIS

[75] Inventors: John A. Main, Nashville, Tenn.; Mark E. Wells, Huntsville, Ala.; Tony S. Keller, Nashville, Tenn.

[73] Assignee: Vanderbilt University, Nashville, Tenn.

[21] Appl. No.: 422,106

[22] Filed: Oct. 16, 1989

[51] Int. Cl.5 .......................... A61F 2/44; A61F 5/04
[52] U.S. Cl. ........................................ 623/17; 606/61
[58] Field of Search ................... 623/16–18; 606/60, 61

[56] References Cited

U.S. PATENT DOCUMENTS

| | | | |
|---|---|---|---|
| 3,426,364 | 2/1969 | Lumb | 623/17 |
| 3,867,728 | 2/1975 | Stubstad et al. | 623/17 |
| 3,875,595 | 4/1975 | Froning | 623/17 |
| 4,349,921 | 9/1982 | Kuntz | 623/17 |
| 4,401,112 | 8/1983 | Rezaian | 623/17 X |
| 4,553,273 | 11/1985 | Wu | 606/61 X |
| 4,554,914 | 11/1985 | Kapp et al. | 606/61 |
| 4,599,086 | 7/1986 | Doty | 623/17 |
| 4,657,550 | 4/1987 | Daher | 623/17 |
| 4,658,809 | 4/1987 | Ulrich et al. | 606/61 |

OTHER PUBLICATIONS

Main, J. A., Design and Evaluation of a Dynamic Vertebral Prosthesis, Master's Thesis, Vanderbilt University, Aug. 1987.
Scoville, W. B., et al, The Use of Acrylic Plastic for Vertebral Replacement, etc., J. Neurosurgery, vol. 27, pp. 274–279 (1967).
Cross, G. O., et al, Acrylic Prosthesis of the Fifth Cervical Vertebra etc., J. Neurosurgery, vol. 35, pp. 112–114 (1971).
Lesoin, F., et al, "Use of Acrylic Prosthesis, etc.," Surgical Neurology, vol. 17, No. 5, pp. 358–362 (1982).
Harrington, K. D., "The Use of Methylmethacrylate for Vertebral-Body Replacement etc.," J. Bone Joint Surg., vol. 63A(1), pp. 36–46 (1981).
Siegal, T., et al, "Vertebral Body Resection etc.," J. Bone Joint Surg., vol. 67A(3), pp. 375–382 (1985).
Ono, K., et al, "Metal Prosthesis of the Cervical Vertabra," J. Neurosurgery, vol. 42, pp. 562–566 (1975).
Rezian, S. M., et al, "Spinal Fixator for Surgical Treatment of Spinal Injury," Orthop. Review, vol. 12, No. 9, pp. 31–41 (1983).
Ma, Y-Z, et al, "The Treatment of Primary Vertebral Tumors by Radical Resection and Prosthetic Vertebral Replacement," Clin. Orthop., vol. 215, pp. 78–90 (1987).

Primary Examiner—Ronald L. Frinks
Attorney, Agent, or Firm—Tilton, Fallon, Lungmus

[57] ABSTRACT

A dynamic prosthetic vertebral body for use in a cavity left by resection of a natural vertebral body and adjacent intervertebral discs. The prosthesis includes a pair of rigid housings joined by a connecting structure that is operable to shift the housings apart into supportive engagement with the healthy vertebral bodies adjacent the site of the resected body. Anchoring pins project outwardly in axial directions from the respective housings for secure fixation to the healthy vertebral bodies. Within the chamber of each housing is a rigid suspension plate surrounded by an elastomeric suspension medium, and the suspension plates of the two housings are joined by the expandable connecting structure. The relative sizes of the suspension plates and the chambers in which they are received allow limited movement of the housings, resulting in a prosthesis that provides the required support but also mimics the dynamics of a normal vertebra and adjacent discs.

14 Claims, 3 Drawing Sheets

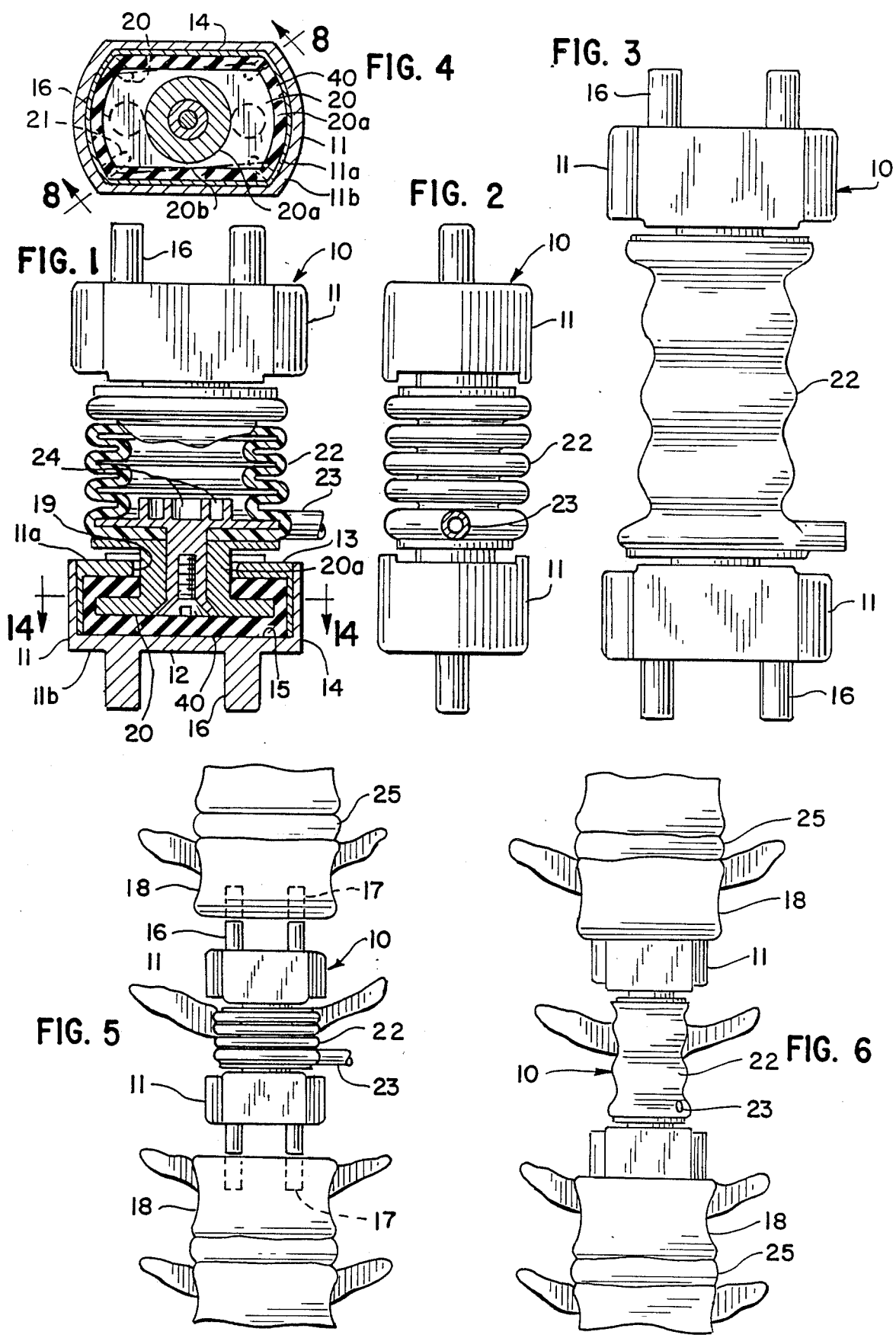

VERTEBRAL PROSTHESIS

BACKGROUND AND SUMMARY

Various implants have been developed to address structural failure of various parts of the spinal column. The prior art with respect to spinal column implants falls into two general categories: intervertebral disc prostheses, and rigid vertebral body prostheses.

Vertebral body prostheses have been disclosed in Pat. such as 3,426,364, 4,401,112, 4,554,914, and 4,599,086. The devices presented in those patents are intended for situations where it is necessary to remove a vertebral body. That, in turn, requires the resection of adjacent intervertebral discs. A problem common to all of such prior devices is that they adequately provide the structure of the removed vertebral body but fail to provide the flexibility of the removed intervertebral discs.

An important aspect of this invention therefore lies in providing a prosthesis for total replacement of a vertebral body and adjacent discs that may be axially expanded during implantation to fit the cavity left by the resection and, when properly in place, provides a stress environment at the prosthesis/bone interface similar to normal in vivo conditions. Specifically, normal ranges of movement are preserved, the prosthesis permitting limited longitudinal flexure, slight compression and expansion, and even a limited degree of torsional movement that at least approximates a normal range.

Briefly, the prosthesis takes the form of a pair of housings, each having end walls and a side wall defining a chamber in which a suspension plate is located. The suspension plates of the two housings are joined by an expandable connector that, in one embodiment of the invention, takes the form of an expandable bellows and, in another embodiment of the invention, comprises a threaded shaft with reverse-direction threads that extends through threaded openings in the two suspension plates. Within each chamber, the suspension plate is surrounded by an elastomeric medium. The medium provides resistance and resilience to movement of the plates within their chambers and the extent of such movement is positively limited by the dimensional differences between each plate and the chamber in which it is carried. Since the outline of each plate conforms with and is only slightly smaller than the outline of the receiving chamber, and since both are non-circular in outline, torsional movement is limited. Because each chamber has an axial dimension substantially greater than the thickness of the plate received in it, each plate may be tipped within its chamber to an extent that, when combined with a similar tipping action of the other suspension plate in its chamber, results in a degree of "bending" that approximates the action of the components of a normal spine. In general, the extent of lateral or sagittal deflection should fall within the range of 3 to 7 degrees measured from the longitudinal midline of the prosthesis, the preferred maximum deflection being about 5 degrees.

The prosthesis also includes means for setting or fixing the spacing between the housings once the prosthesis has been inserted and expanded into supportive contact with the healthy adjoining vertebrae. In the bellows-equipped embodiment, the setting means take the form of a fluid capable of hardening after being injected into the bellows to cause expansion of the prosthesis. In the embodiment in which the expansion means take the form of a threaded shaft, the setting means comprises a pair of jam nuts that may be screwed into tight frictional engagement with the inwardly (proximally) facing surfaces of the two suspension plates.

Other features, advantages, and objects of the invention will become apparent from the specification and drawings.

DRAWINGS

FIG. 1 is a side elevational view, taken partly in section, showing a vertebral prosthesis embodying the present invention, the prosthesis being depicted in collapsed condition.

FIG. 2 is another side elevational view of the collapsed prosthesis.

FIG. 3 is an elevational view similar to FIG. 1 but showing the prosthesis in expanded condition.

FIG. 4 is a sectional view taken along line 4—4 of FIG. 1.

FIGS. 5 and 6 are schematic views depicting implantation of the prosthesis and showing the prosthesis before and after expansion.

DETAILED DESCRIPTION OF PREFERRED EMBODIMENTS

Figure 7:
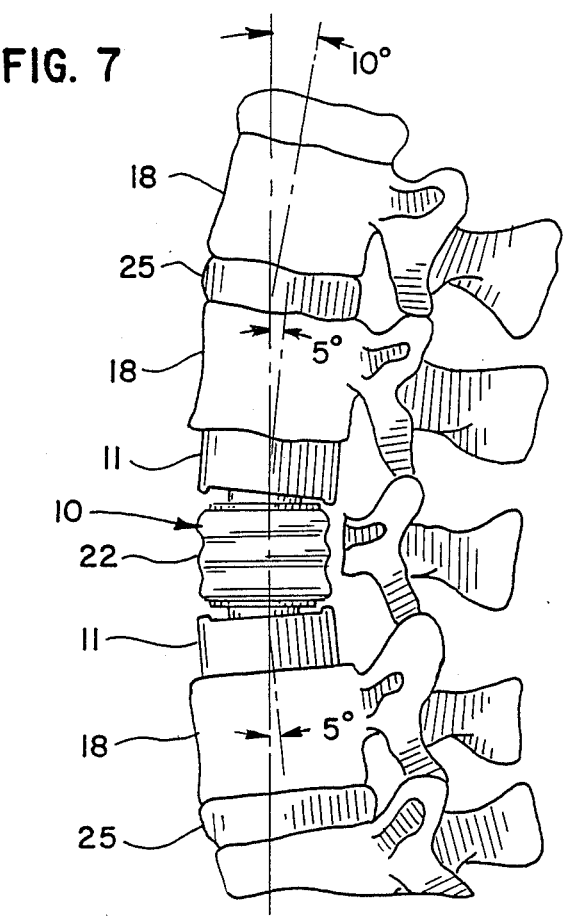
FIG. 7 is a lateral view illustrating the range of bending action permitted by the prosthesis.

Referring to the drawings, the numeral 10 generally designates a vertebral prosthesis having a pair of head units or housings 11 formed of rigid biocompatible material such as, for example, stainless steel or titanium. Each housing is composed of an inner section 11a and an outer section 11b, the two sections being nested together as shown in FIG. 1 and being permanently secured together by any suitable means. Each housing includes a distal end wall 12, a proximal end wall 13, and a side wall 14, together defining a chamber 15.

The distal end wall 12 includes anchoring means in the form of two or more cylindrical extensions or pins 16. The integral pins are adapted to be received in holes 17 drilled into the exposed faces of adjoining healthy vertebral bodies 18 at the time of surgery (FIG. 5). It is to be understood that section 11b of the housing may be foraminous to facilitate and promote bone ingrowth. As well known in the art, sintered metal surfaces have been found particularly effective for that purpose. While a detailed discussion is believed unnecessary, it will be appreciated that the integral pins 16 are particularly important for initial fixation and for immobilizing housing 11 with respect to the adjoining vertebrae so that bone ingrowth may ultimately occur, at which time the ingrowth becomes a major factor in maintaining fixation. Another major factor in achieving and maintaining fixation is believed to be the limited yieldability of the prosthesis which, by mimicking the action of the replaced components, reduces the stresses at the bone/prosthesis interfaces.

Figure 8:
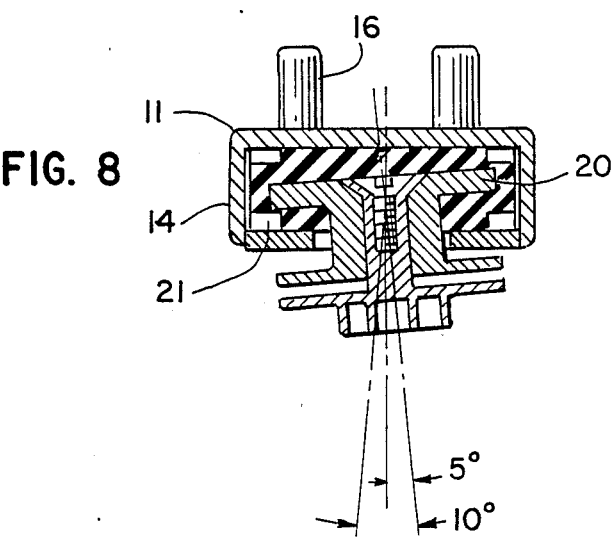
FIG. 8 is a sectional view taken generally along line 8—8 of FIG. 4 but showing the suspension plate in a fully deflected position.
Figure 9:
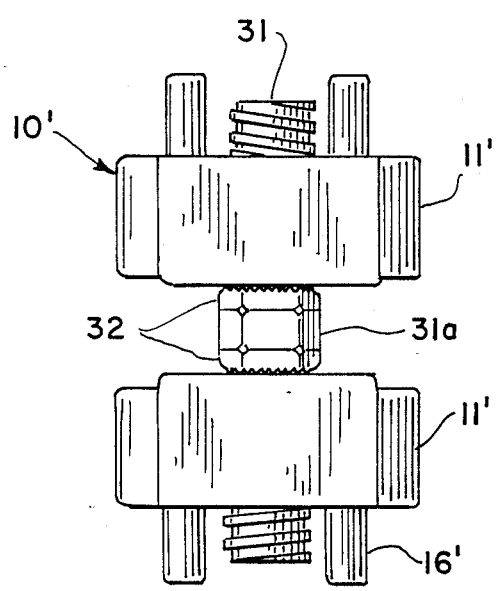
FIG. 9 is an elevational view of a prosthesis constituting a second embodiment of the invention, the prosthesis being shown in retracted condition.
Figure 10:
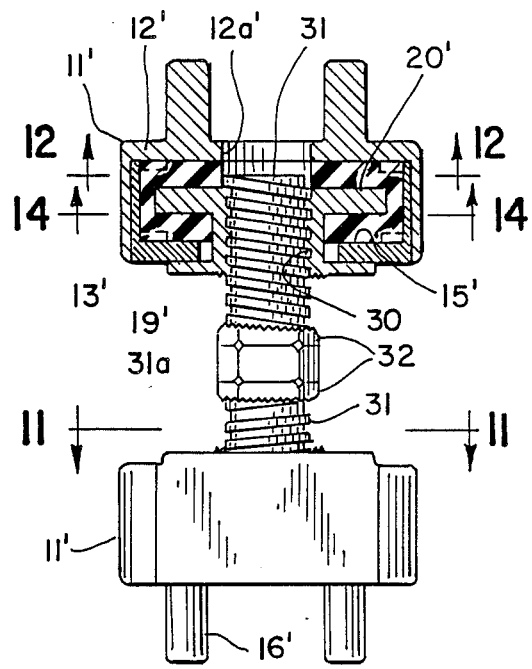
FIG. 10 is an elevational view, taken partly in section, showing the prosthesis of FIG. 9 in expanded condition.
Figure 11:
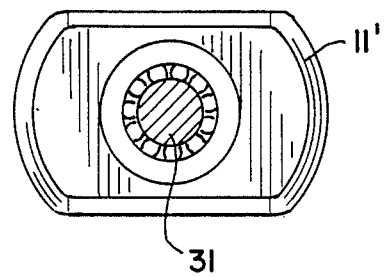
FIG. 11 is a sectional view taken along line 11—11 FIG. 10.
Figure 13:
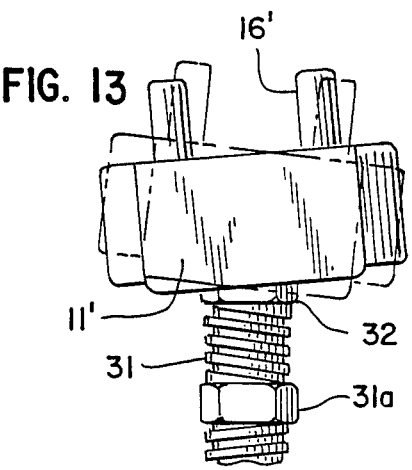
FIG. 13 is a fragmentary elevational view depicting the range of deflection permitted by the prosthesis construction of FIGS. 9-12.
Figure 12:
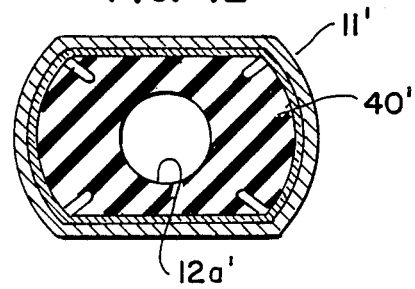
FIG. 12 is a sectional view along line 12—12 of FIG. 10.
Figure 14:
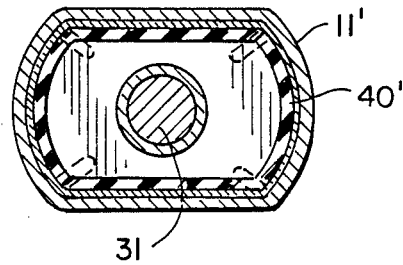
FIG. 14 is a sectional view taken along line 14—14 of FIG. 10.

The proximal end wall 13 of each housing 11 has an axial opening 19. The stem 20a of a suspension plate or member 20 extends through that opening. FIG. 1 reveals that the thickness or axial dimension of plate 20 is substantially less than the axial dimension of cavity 15. Also, while the perimeter of the suspension plate generally follows the contour of the cavity, it is slightly smaller in outline. As a result, a tipping action of the plate 20 may take place within cavity 15, such action being depicted in FIG. 8. The extent of maximum deflection from the longitudinal midline or axis should fall within the range of 3 to 7 degrees, with 5 degrees being shown. Since such angular measurement is taken from the normal midline when the plate and housing are coaxially disposed, it is believed evident that the total maximum extent of tipping movement, measured from one extreme to the other, would be within the range of 6 to 14 degrees, with 10 degrees being illustrated. Deflection is limited by engagement between the peripheral of the suspension plate 20 and the end walls 12 and 13 of housing 11. If desired, the end walls may be provided with deflection stops 21 projecting inwardly from the corners of the cavity as shown most clearly in FIGS. 8 and 4.

Torsional movement of plate 20 is limited by the narrow spacing between the periphery of the plate and the interior surfaces of the cavity and by the further fact that both the plate and cavity are non-circular in outline. As depicted in FIG. 4, the plate has a pair of parallel side edges 20b and arcuate edges 20c at opposite ends. The curvature of edges 20c is concentric with the axis of the housing so that torsional movement is limited essentially by contact between side edges 20b and the side wall 14 of the housing. FIG. 4 depicts in broken lines the maximum extent of relative rotation or torsional movement of the suspension plate 20 and housing 11. In general, the maximum extent of relative rotation measured in one direction from a neutral position should fall within the range of 5 to 10 degrees.

Of particular significance is the fact that plate 20 is surrounded and suspended in chamber 15 by an elastomeric medium 40. Silicone rubber of a durometer measurement of 70 on the C scale has been found effective, but other elastomeric materials having similar properties may be used. The elastomeric material, in addition to functioning as a suspending medium, exerts forces that tend to restrain and cushion relative movement of plate 20 and housing 11. It also provides an axial cushion with respect to spinal extension and compression in a manner that tends to mimic the action of natural intervertebral discs. Such action is again believed important in maintaining secure fixation between the distal end walls 12 and pins 16 and the adjoining natural vertebrae.

The two suspension plates or members 20 are interconnected by expandable bellows 22 formed of any suitable material having sufficient flexibility to permit expansion of the bellows into the condition shown in FIG. 3 and also having properties that render it compatible in a biological environment. Inlet stem 23 permits the injection of fluid into the bellows to cause axial expansion of the prosthesis. The injection fluid is one that must be capable of hardening to form a rigid mass.

Acrylic cements have been used effectively, but other materials having similar properties are well known in the art. Since the inner or proximal end of each suspension plate is provided with channels and recesses 24 (FIG. 1), the two suspension plates and the mass of hardened material within the bellows become firmly locked together when the core material has hardened or cured. Therefore, when the fluid responsible for bellows expansion has solidified, with the prosthesis in expanded condition as depicted in FIGS. 3 and 6, the two housings 11 are secured against relative movement except to the extent allowed by axial movement, tipping movement, and limited torsional movement of suspension plates 20 in housings 11.

FIG. 5 shows the prosthesis 10 at the time of implantation, after resection of a vertebral body and its adjoining discs and following formation of holes 17 in the opposing faces of the adjacent healthy vertebrae 18. Following alignment of pins 16 with openings 17, the bellows 22 is expanded into the condition depicted in FIG. 6 and the injected fluid is allowed to set or harden, at which time the stem 23 may be severed from the bellows. In lateral view, the prosthesis would appear as somewhat schematically depicted in FIG. 7. It will be observed that the sagittal flexure between adjacent natural vertebrae 18 separated by a natural intervertebral disc 25 is 5 degrees, matching the maximum deflection at each end of the prosthesis.

In the embodiment of FIGS. 9-14, the housings 11' are similar to those already described except that the distal end walls 12' are provided with openings 12a' axially aligned with openings 19' in proximal end walls 13'. Suspension plates 20'are suspended in chambers 15' in the same manner previously described. Therefore in terms of axial compression and expansion, angular deflection, and torsional movement, the two embodiments are indistinguishable.

The difference lies in the expansion means for shifting the two housings 11' apart and for locking or fixing such housings in their selected positions of expansion. In the second embodiment, each suspension plate 20' has a threaded opening or bore 30 that threadedly receives an end portion of screw shaft 31. The two end portions of the shaft are threaded in opposite directions so that when the central portion 31a is gripped and rotated by a suitable tool (not shown), the two suspension plates 20' and the housings 11' carried by them will be shifted axially away from each other.

Two jamming nuts 32 are disposed alongside the central portion 31a when the prosthesis is in its original contracted state but, after being expanded into contact with adjoining vertebrae, the jam nuts are screwed away from the central portion 31a and into tight frictional engagement With the proximal surfaces of suspension plates 20'. Preferably, serrations are formed on the opposing faces of the jam nuts 32 and the contacting surfaces of suspension plates 20' to prevent relative rotation of the housings and shaft.

While in the foregoing we have disclosed embodiments of the invention in considerable detail, it will understood by those skilled in the art that many of these details may be varied without departing from the spirit and scope of the invention.

We claim:

1. A vertebral prosthesis for total replacement of a resected vertebral body and adjoining discs, comprising a pair of housings having side walls, distal end walls with outer surfaces facing in opposite directions, and proximal end walls having openings therein and having outer surfaces disposed in opposition; said side and end walls of each housing defining a chamber; anchoring means projecting distally from each distal end wall for locking engagement with a natural vertebral body adjacent thereto; a suspension plate in each chamber spaced from said side and end walls for limited relative movement of said plate and the housing defining said chamber; an elastomeric suspension medium surrounding said suspension plate in each chamber; and expandable connecting mean projecting through said openings in said proximal end walls and adjustably connecting said suspension plates of said pair of housings for selectively increasing the distance between said housings.

2. The prosthesis of claim 1 in which said connecting means includes setting means for fixing the spacing between said housings at selected distances.

3. The prosthesis of claim 2 in which said connecting means comprises an expandable bellows extending between and joining said suspension plates; said bellows including an expansion chamber having an inlet for the injection of fluid into said bellows for selectively increasing the spacing between said housings.

4. The prosthesis of claim 3 in which said setting means comprises a fluid capable of hardening into a solid mass following injection of said fluid into said bellows.

5. The prosthesis of claim 4 in which said fluid is an acrylic cement.

6. The prosthesis of claim 2 in which said connecting means comprises a screw shaft having opposite ends extending into said housings through said openings; each suspension plate having a threaded opening receiving one end portion of said screw shaft; and means provided by said shaft between said end portions for attaching a driving tool for manual rotation of said shaft.

7. The prosthesis of claim 6 in which said setting means comprises a pair of jam nuts threadedly mounted upon said end portions of said shaft for fictionally engaging said suspension plates and for locking said shaft against rotation relative thereto.

8. The prosthesis of claim 7 in which said jam nuts and said suspension plates have serrated contacting surfaces.

9. The prosthesis of claim 1 in which each of said suspension plates is non-circular in outline.

10. The prosthesis of claim 9 in which each suspension plate has edge surfaces spaced slightly inwardly from said walls of said housing to permit limited torsional movement of said suspension plate in said chamber.

11. The prosthesis of claim 10 in which said walls of said housing limit relative rotational movement of said plate to an angular distance within the range of 5 to 10 degrees.

12. The prosthesis of claim 1 in which each suspension plate has proximal and distal surfaces facing inside surfaces of said end walls of said housing; said proximal and distal surfaces of said suspension plate being normally maintained in spaced relation with respect to said inside surfaces by said elastomeric suspension medium; the spacing between said end walls and said distal and proximal surfaces of said suspension plate limiting the extent of tipping movement of each plate in said chamber to a maximum angular deflection within the range of 3 to 7 degrees measured from a neutral midline.

13. The prosthesis of claim 12 in which said maximum angular deflection is approximately 5 degrees.

14. The prosthesis of claim 12 in which said end walls of said housing provide deflection stops within said chamber for deflection-limiting engagement with said suspension plate.

* * * * *